US012502339B2

(12) United States Patent
Swaile et al.

(10) Patent No.: US 12,502,339 B2
(45) Date of Patent: Dec. 23, 2025

(54) FOAM COMPOSITIONS

(71) Applicant: The Procter & Gamble Company, Cincinnati, OH (US)

(72) Inventors: David Frederick Swaile, Cincinnati, OH (US); Barbara Marie Modafari, Mason, OH (US); Jorge Max Sunkel, West Chester, OH (US); Jianwei Zhang, Mason, OH (US); Kerry Andrew Vetter, Cincinnati, OH (US); Richard Oryszczak, Palatine, IL (US); Stephen J. Provancal, Elmhurst, IL (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/734,188

(22) Filed: May 2, 2022

(65) Prior Publication Data

US 2022/0354758 A1 Nov. 10, 2022

Related U.S. Application Data

(60) Provisional application No. 63/183,142, filed on May 3, 2021.

(51) Int. Cl.
*A61K 8/04* (2006.01)
*A61K 8/06* (2006.01)
(Continued)

(52) U.S. Cl.
CPC .............. *A61K 8/046* (2013.01); *A61K 8/062* (2013.01); *A61K 8/19* (2013.01); *A61K 8/26* (2013.01);
(Continued)

(58) Field of Classification Search
None
See application file for complete search history.

(56) References Cited

U.S. PATENT DOCUMENTS

| | | | |
|---|---|---|---|
| 153,759 | A | 8/1874 | Blatt |
| 160,098 | A | 2/1875 | Hoyle et al. |

(Continued)

FOREIGN PATENT DOCUMENTS

| | | | |
|---|---|---|---|
| DE | 102011089430 | A1 | 8/2012 |
| EP | 1557160 | A1 | 7/2005 |

(Continued)

OTHER PUBLICATIONS

"1,2 Octanediol (Caprylyl Glycol) & 1,2 Hexanediol"—an internet article obtained from the website: https://www.kumarorganic.net/Company/Blog-details.php?blogcode=KOP201901252CK1U5V5ZB (date unknown).*

(Continued)

*Primary Examiner* — Sin J Lee
(74) *Attorney, Agent, or Firm* — Alexandra S. Anoff

(57) ABSTRACT

A foaming antiperspirant or deodorant composition comprising: a. an oil in water emulsion comprising: i. a first oil phase comprising one or more emollients; ii. a second oil phase comprising one or more emollients; wherein the second oil phase emollients have at most 5% solubility in the first oil phase emollients; iii. an antiperspirant or deodorant active; iv. one or more nonionic emulsifier; and v. a fragrance; and b. at most about 15%, by weight of the composition, of a blowing agent.

13 Claims, 5 Drawing Sheets

(51) Int. Cl.

| | |
|---|---|
| ***A61K 8/19*** | (2006.01) |
| ***A61K 8/26*** | (2006.01) |
| ***A61K 8/33*** | (2006.01) |
| ***A61K 8/34*** | (2006.01) |
| ***A61K 8/37*** | (2006.01) |
| ***A61K 8/39*** | (2006.01) |
| ***A61K 8/86*** | (2006.01) |
| ***A61K 8/891*** | (2006.01) |
| ***A61Q 15/00*** | (2006.01) |

(52) U.S. Cl.

CPC ................ *A61K 8/33* (2013.01); *A61K 8/342* (2013.01); *A61K 8/37* (2013.01); *A61K 8/39* (2013.01); *A61K 8/86* (2013.01); *A61K 8/891* (2013.01); *A61Q 15/00* (2013.01); *A61K 2800/87* (2013.01)

(56) References Cited

U.S. PATENT DOCUMENTS

| | | | | |
|---|---|---|---|---|
| D139,381 | S | 11/1944 | Harris | |
| D208,735 | S | 9/1967 | Rahn et al. | |
| D231,087 | S | 4/1974 | Edwards | |
| D240,112 | S | 6/1976 | O'Neil et al. | |
| D240,711 | S | 7/1976 | Angleman et al. | |
| 4,019,657 | A | 4/1977 | Spitzer et al. | |
| 4,174,386 | A | 11/1979 | Marra et al. | |
| D281,228 | S | 11/1985 | Grip et al. | |
| 4,991,751 | A | 2/1991 | Naku | |
| D315,292 | S | 3/1991 | Seager | |
| 5,226,563 | A | 7/1993 | Coggiola | |
| D351,337 | S | 10/1994 | Bonnema et al. | |
| 5,618,515 | A | 4/1997 | Singh et al. | |
| D388,320 | S | 12/1997 | Lamb | |
| D395,597 | S | 6/1998 | Lamb | |
| 5,813,785 | A | 9/1998 | Baudin et al. | |
| 5,899,623 | A | 5/1999 | De Laforcade | |
| 6,032,836 | A | 3/2000 | Hiscocks et al. | |
| D422,902 | S | 4/2000 | Kikuchi | |
| D437,548 | S | 2/2001 | Desgrippes et al. | |
| D445,337 | S | 7/2001 | Croft et al. | |
| D447,057 | S | 8/2001 | Bezek et al. | |
| D447,693 | S | 9/2001 | Warner et al. | |
| D448,281 | S | 9/2001 | Thibiant et al. | |
| D452,823 | S | 1/2002 | Bezek et al. | |
| D501,133 | S | 1/2005 | Schuller et al. | |
| D535,563 | S | 1/2007 | Martin | |
| D536,220 | S | 2/2007 | Sandberg | |
| D538,178 | S | 3/2007 | Desgrippes et al. | |
| D554,505 | S | 11/2007 | Gilbert | |
| D569,253 | S | 5/2008 | Cracchiolo | |
| D582,278 | S | 12/2008 | Bourne | |
| D610,459 | S | 2/2010 | Nagata | |
| D616,261 | S | 5/2010 | Lundstrom | |
| D616,262 | S | 5/2010 | Lundstrom | |
| D627,603 | S | 11/2010 | Eyal | |
| 7,905,673 | B2 | 3/2011 | Swaile et al. | |
| D639,166 | S | 6/2011 | Carreno | |
| D639,660 | S | 6/2011 | Carreno | |
| D639,662 | S | 6/2011 | Riguzzi | |
| D640,136 | S | 6/2011 | Liba | |
| D642,852 | S | 8/2011 | Sheppard et al. | |
| D647,802 | S | 11/2011 | Bunce et al. | |
| D653,112 | S | 1/2012 | White et al. | |
| 8,119,109 | B2 | 2/2012 | Tamarkin et al. | |
| D666,912 | S | 9/2012 | Kawai | |
| D671,836 | S | 12/2012 | Demarco | |
| D687,711 | S | 8/2013 | Demarco | |
| D700,060 | S | 2/2014 | Trevisan | |
| D714,162 | S | 9/2014 | Kang | |
| D717,654 | S | 11/2014 | Aular | |
| D739,251 | S | 9/2015 | Kawai | |
| D746,691 | S | 1/2016 | Uchida | |
| 9,296,550 | B2 | 3/2016 | Smith | |
| D758,204 | S | 6/2016 | Hwang | |
| D759,501 | S | 6/2016 | Hwang | |
| D786,079 | S | 5/2017 | Ibáñez et al. | |
| D820,110 | S | 6/2018 | Burrowes et al. | |
| D858,198 | S | 9/2019 | Hsu | |
| 10,526,133 | B2 | 1/2020 | Zeik et al. | |
| D922,200 | S | 6/2021 | Dietvorst et al. | |
| D934,689 | S | 11/2021 | Berg et al. | |
| D938,282 | S | 12/2021 | Scott | |
| D951,094 | S | 5/2022 | Valcke | |
| 2004/0197295 | A1 | 10/2004 | Riedel et al. | |
| 2005/0123494 | A1 * | 6/2005 | Swaile .................. | A61K 8/046 424/65 |
| 2010/0217176 | A1 | 8/2010 | Carrara et al. | |
| 2012/0138699 | A1 | 6/2012 | Prischak | |
| 2014/0086848 | A1 | 3/2014 | Tamarkin et al. | |
| 2014/0323993 | A1 | 10/2014 | Wilcox et al. | |
| 2017/0247170 | A1 | 8/2017 | Bilton et al. | |
| 2020/0000686 | A1 * | 1/2020 | Swaile .................. | A61K 8/361 |
| 2020/0148459 | A1 | 5/2020 | Bartolucci et al. | |

FOREIGN PATENT DOCUMENTS

| | | | | |
|---|---|---|---|---|
| EP | 3162356 | A1 | 5/2017 | |
| GB | 90038700130001 | | 4/2017 | |
| JP | 2010254312 | A | 11/2010 | |
| WO | WO-9401511 | A1 * | 1/1994 | ............. A61K 8/046 |
| WO | 03053388 | A1 | 7/2003 | |
| WO | 2005048966 | A1 | 6/2005 | |
| WO | 2008038140 | A2 | 4/2008 | |
| WO | 2012131320 | A2 | 10/2012 | |
| WO | D217243002 | | 5/2022 | |
| WO | D217243003 | | 5/2022 | |

OTHER PUBLICATIONS

"DOWSILTM5562 Carbinol Fluid"—a Technical Data Sheet obtained from the website: https://www.dow.com/en-us/pdp.dowsil-5562-carbinol-fluid.04019849z.html#tech-content (date unknown).*

Technical Data sheet by US BIological Life Sciences (obtained from the website: https://www.usbio.net/biochemicals/010188/Dimethicone/data-sheet ) (date unknown).*

Secret Weightless Dry Spray Antiperspirant for Women; Available online:https://www.amazon.com/Secret-Antiperspirant-Depdorant-Women-Spray/dp/B09NPS16JW/ref=sr_1_2; dated Aug. 8, 2022, 7 pages.

All Office Actions, U.S. Appl. No. 29/759,855, filed Nov. 25, 2020.

All Office Actions; U.S. Appl. No. 17/734,193, filed May 2, 2022.

All Office Actions; U.S. Appl. No. 17/735,389, filed May 3, 2022.

All Office Actions; U.S. Appl. No. 29/781,997, filed May 3, 2021.

Unpublished U.S. Appl. No. 17/734,193, filed May 2, 2022, to David Frederick Swaile et al.

Unpublished U.S. Appl. No. 17/735,389, filed May 3, 2022, to Matthew John Martin et al.

PCT Search Report and Written Opinion for PCT/US2022/027225 dated Oct. 13, 2022, 12 pages.

U.S. Appl. No. 29/759,855, filed Nov. 25, 2020, Matthew Corey Cataudella et al..

U.S. Appl. No. 29/781,997, filed May 3, 2021, Matthew Corey Cataudella et al.

Liquefied Gas, Health & Safety Glossary, Retrieved from Internet: https://www.ecoonline.com/en-us/glossary/liquefied-gas#:--:text=Liquefied%20gasses%20are%20gases%20that,%2C%20propane%2C%20and%20carbon%20dioxide, 4 pages.

* cited by examiner passing example on left, failing example on right

FOAM COMPOSITIONS

TECHNICAL FIELD

One aspect of the invention relates generally to foam compositions containing an antiperspirant and/or deodorant active.

BACKGROUND OF THE INVENTION

Antiperspirant and deodorant products deliver materials to the axilla skin that reduce eccrine gland sweating, control the growth of odor causing bacteria, and provide a fragrance benefit. These products are known in many forms, including roll-ons, gels, creams, sticks, sprays, and foams. Consumers choose their form based on personal requirements for application experience (rub on or spray), application feel (i.e. wet or dry), product performance for odor and wetness control, and the appearance of product residue on skin or clothing. In general, there is a desire from consumers to have a product that has a convenient application process, dries quickly on skin, creates little to no white residue on skin or clothes, provides all day odor and wetness control, and delivers a pleasant fragrance experience that lasts all day.

Within the set of known products, foams are less common but can provide the above desired benefits without some of the negatives of other forms. Aqueous foam products typically have a density of less than 0.2 grams/ml, which allows users to easily spread a lower product dose across the entire axilla. Often foam products are used at a dose of 0.1-0.3 grams per axilla, which is lower than the 0.3-0.6 gram dose of other rub on products like roll-ons, sticks and exams. The lower dose of the foam reduces the drying time, even versus gels, which also contain water. Another benefit of foams is that they typically do not contain a high level of structurant waxes like many sticks. Without the high level of structurant and applied at lower doses, the foams reduce the amount of visible residue that can be seen on skin or transferred to clothing. Sprays can deliver low doses that cover the axilla, but they often create a gassy cloud during application that is undesirable to many consumers. Foam products do not create this cloud during application.

One reason that foams have been less popular to date is the complexity of delivering a stable foam formulation that is easily delivered to the skin. A foam product must be stable enough to easily be rubbed on the skin from a hand held device. In addition, the foam product must contain actives that are effective at low dosages, be capable of delivering enough fragrance to provide all day noticeability and odor masking, deliver emollients that provide a dry feel and lubricate the skin throughout the day, comprise a minimum level of foaming emulsifiers/surfactants to prevent skin irritation, and finally, the foam product must have a low enough level of blowing agent to prevent the formulation from aerosolizing during dosing.

Thus, there is a continuing need for stable and efficacious antiperspirant and deodorant foam compositions.

SUMMARY OF THE DISCLOSURE

A foaming antiperspirant or deodorant composition comprising: a. an oil in water emulsion comprising: i. a first oil phase comprising one or more emollients; ii. a second oil phase comprising one or more emollients; wherein the second oil phase emollients have at most 5% solubility in the first oil phase emollients; iii. an antiperspirant or deodorant active; iv. one or more nonionic emulsifier; and v. a fragrance; and b. at most about 15%, by weight of the composition, of a blowing agent.

BRIEF DESCRIPTION OF THE DRAWINGS

While the specification concludes with claims, it is believed that the same will be better understood from the following description taken in conjunction with the accompanying drawings wherein like numbers illustrate like elements throughout the views and in which:

DETAILED DESCRIPTION

Figure 1A:
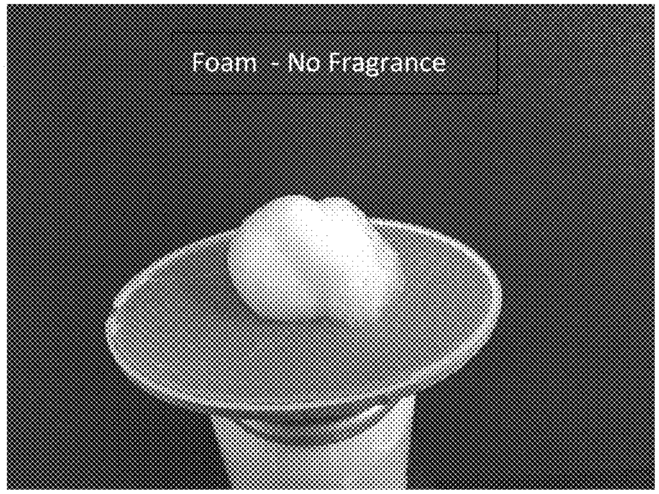
FIGS. 1*a* and 1*b* are photographs showing the impact of fragrance on foam quality for an emulsion.

A device, container, composition, blowing agent, etc. may comprise, consist essentially of, or consist of, various combinations of the materials, features, structures, and/or characteristics described herein.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments of the present invention, all percentages are by weight of the antiperspirant or deodorant composition (or formulation), unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. The term "molecular weight" or "M.Wt." as used herein refers to the number average molecular weight in Daltons unless otherwise stated.

The term "antiperspirant composition" refers to any composition containing an antiperspirant active and which is intended to be applied onto skin. The term "deodorant composition" refers to any composition containing a deodorant active and which is intended to be applied onto skin.

The term "at the time of making" refers to a characteristic (e.g., viscosity) of a raw material ingredient just prior to mixing with other ingredients.

The term "container" and "device" and derivatives thereof refers to the package that is intended to store and dispense an antiperspirant or deodorant composition. A container or device may typically comprise a reservoir for storing the antiperspirant or deodorant composition, a valve for controlling flow of the antiperspirant or deodorant composition, and an actuator by which a user can actuate the valve.

The term "substantially free of" refers to an amount of a material that is less than 1%, 0.5%, 0.25%, 0.1%, 0.05%, 0.01%, or 0.001% by weight of an antiperspirant composition. "Free of" refers to no detectable amount of the stated ingredient or thing.

The term "total fill" or "total fill of materials" refers to the total amount of materials added to or stored within a reservoir(s) of a container. For example, total fill includes the blowing agent and antiperspirant or deodorant composition stored within a device after completion of filling and prior to first use.

The term "viscosity" means dynamic viscosity (measured in centipoise, cPs, or Pascal-second, Pa·s) or kinematic viscosity (measured in centistokes, cst, or $m^2/s$) of a liquid at approximately 25° C. and ambient conditions. Dynamic viscosity may be measured using a rotational viscometer, such as a Brookfield Dial Reading Viscometer Model 1-2 RVT available from Brookfield Engineering Laboratories (USA) or other substitutable model known in the art. Typical Brookfield spindles which may be used include, without limitation, RV-7 at a spindle speed of 20 rpm, recognizing that the exact spindle may be selected as needed by one skilled in the art. Kinematic viscosity may be determined by dividing dynamic viscosity by the density of the liquid (at 25° C. and ambient conditions), as known in the art.

Oil in Water Emulsion

The antiperspirant and deodorant foam compositions of the present invention may comprise an oil in water emulsion. An oil phase in these emulsions may comprise an emollient, an emulsifier and optionally other ingredients such as, but not limited to, co-emulsifiers, fragrances, deodorant actives, skin conditioners, or other oil soluble ingredients. Emollients in the present invention are water insoluble liquids that smooth, soften, or lubricate the skin and will typically comprise more than 30% of an oil phase. The role of the oil phase in the foam composition is multifold. An oil phase must be water insoluble enough to provide a stable emulsion, not interfere with the antiperspirant active, provide a solvent system for the fragrance, and provide a lubricious soft feel to the consumer's skin throughout the day. Moreover, it must not interfere with the formation of a stable foam that is easily rubbed on the skin. The present inventors have unexpectedly discovered that the complexity of this role is best accomplished with more than one oil phase, wherein the different oil phases remain segregated during the life of the product. Said differently, having multiple disparate phases allows each phase to be focused on specific goals, wherein the combination of phases provides all the desired benefits. Moreover, the present inventors have surprisingly found that creating and stabilizing more than one oil phase is best accomplished by creating oil phases with limited to no solubility in each other. The limited solubility allows the different oil phases to remain segregated both during the formation of the multiple emulsions (often done at elevated temperatures (i.e., 40° C.-60° C.)) and through extended storage of the products (i.e., more than 1 year). Furthermore, the inventors have found that having less than or at most about 5% solubility of the emollients of the second oil phase into the emollients of the first oil phase is sufficient to provide the desired stability, with less than or at most about 1% solubility being preferred, and less than or at most about 0.5% being more preferred. Specifically, the emollient(s) of the second oil phase may have less than or at most about 5% solubility in the emollient(s) of the first oil phase; in some embodiments the emollient(s) of the second oil phase may have less than or at most about 1% solubility in the emollient (s) of the first oil phase; and in some embodiments, the emollient(s) of the second oil phase may have less than or at most about 0.5% solubility in the emollient(s) of the first oil phase. The test method for determining oil phase emollient solubility is detailed in the Test Method section herein. While the first and second oil phases may comprise more than just emollients, having the emollient(s) of the second oil phase have less than or at most about 5% solubility in the emollient(s) of the first oil phase assures that the first and second oil phases remain separate, as the emollients drive the solubility of the oil phases.

First Oil Phase Emollients

Figure 1B:
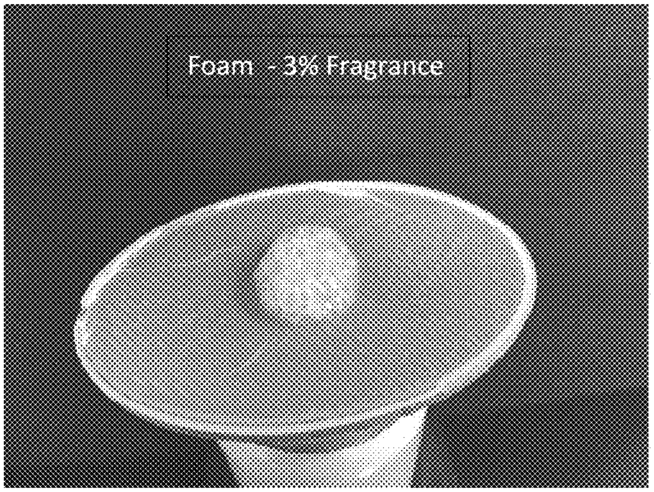

The first oil phase may comprise an emollient or mixture of emollients that typically are a solvent for the fragrance in the composition. If the fragrance is not well solubilized by the emollient in the oil phase, it can become associated with the polar portion of the emulsifier, thereby reducing both emulsion stability and foam quality. FIG. 1 shows the impact of fragrance on foam quality for an emulsion. Both foams in FIGS. 1*a* and 1*b* use 100 cst dimethicone as an emollient, which is a poor fragrance solvent. As can be seen in the figure, the product without fragrance in FIG. 1*a* provides a desirable foam appearance, while the product with fragrance in FIG. 1*b* creates a less stable foam that has an undesirable wet appearance. So in order to incorporate fragrance into the first oil phase without reducing the foam quality, certain emollients may be used that are good fragrance solubilizers. Water insoluble emollients that are good fragrance solvents often have moderate polarity that can be characterized by having a Hildebrand solubility parameter from about 14 to about 22 $(MPa)^{0.5}$. Often values lower than that can be soluble in the dimethicone emollient in the second oil phase, while values higher than that can be too polar or water soluble to create a stable oil in water emulsion. A description of solubility parameters and means for determining them are described by C. D. Vaughan, "Solubility Effects in Product, Package, Penetration and Preservation" 103 Cosmetics and Toiletries 47-69, October 1988; and C. D. Vaughan, "Using Solubility Parameters in Cosmetics Formulation", 36 J Soc. Cosmetic Chemists 319-333, September/October, 198, which descriptions are incorporated herein by reference. Additionally, it may be desirable for emollients in the first oil phase to have a molecular weight greater than about 500 daltons to reduce skin penetration of the fragrance, thereby maintaining the ability of the fragrance to volatilize and provide the desired long-lasting and pleasant fragrance experience.

In some cases, the high molecular weight emollients of the first oil phase may have a molecular weight of at least about 500 Daltons, or at least about 750 Daltons, in some other cases, at least about 1000 Daltons, and in some other cases, at least about 1500 Daltons. The emollients used may be liquid. Suitable moderate polarity high molecular weight or liquid emollients may include, but are not limited to, propoxylated fatty alcohols, propoxylated fatty acids, ethoxylated propoxylated fatty alcohols, ethoxylate propoxylated fatty acids, and combinations thereof. Suitable high molecular weight or liquid emollients may include propoxylated fatty acids and propoxylated fatty alcohols, such as PPG-15 stearyl ether, PPG-11 Stearyl ether, PPG-15 Lauryl ether, PPG-11 Lauryl ether, PPG-15 myristyl ether, PPG-11 myristyl ether, PPG-14 butyl ether, PPG-30 butyl ether, and PPG-30 Cetyl ether. As used herein, fatty alcohol or fatty acid chains of the high molecular weight emollients include linear or branched alkyl chains with more than 4 carbon atoms. Typical chain lengths are from 4 to 28 atoms, with some embodiments having chain lengths of 4 to 18 carbon atoms. Moreover in some embodiments, the emollient will have a viscosity of less then 500 cps, less then 200 cps, or less than 100 cps. This viscosity range is capable of providing a light feel on skin which is desirable by some consumers.

The emollients in the first oil phase may comprise from about 5% to about 30%, by weight, of the antiperspirant or deodorant composition. In some embodiments, the antiperspirant and deodorant composition may comprise from about 10% to about 20%, by weight, of the antiperspirant or deodorant composition. Choice of the amount of the one or more emollients in the first oil phase is dependent on a variety of factors including, but not limited to, desired skin feel, foam appearance, and fragrance concentration. To provide adequate fragrance dissolution, the ratio of emollient in the first oil phase to fragrance in the first oil phase may be at least 1:1, or may range from about 1:1 to about 10:1, in some embodiments from about 1:1 to about 7:1, in other embodiments from about 1:1 to about 4:1, in other embodiments from about 3:1 to about 7:1, and in still other embodiments from about 1:1 to about 3:1. In some embodiments, the antiperspirant and deodorant composition may comprise from about 5% to about 30%, by weight of the composition, of first oil phase emollient(s) selected from or selected from the group consisting of propoxylated fatty alcohols, propoxylated fatty acids, ethoxylated propoxylated fatty alcohols, ethoxylated propoxylated fatty acids, or combinations thereof, that have a molecular weight of at least about 500 Daltons. In some embodiments, the antiperspirant and deodorant composition may comprise from about 5% to about 20%, by weight of the composition, or from about 10% to about 20%, by weight of the composition, of one or more first oil phase emollients having a molecular weight of at least about 750 Daltons, or of liquid emollients.

Second Oil Phase Emollients

The second oil phase comprises a silicone, specifically dimethicone, also referred to as polydimethylsiloxane, emollient that is not soluble in the first oil phase as shown by the emollient solubility test described herein. In some embodiments, the dimethicone can be blended with other dimethicone soluble emollients wherein the mixture is not soluble in the first oil phase as shown by the solubility test described herein. Dimethicone emollients provide a smooth feel throughout the day and reduce stickiness that can result from certain antiperspirant or deodorant actives. Dimethicone emollients generally have the following structure, where n is number of 2 or more:

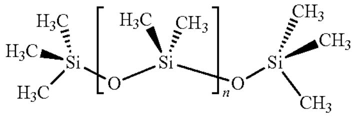

As n increases, the viscosity of the dimethicone emollient also increases. Moreover, as n increases, there is a general reduction in solubility in the organic emollients of the first oil phase. It then will be appreciated that a dimethicone emollient may be further characterized by, optionally, its viscosity, its molecular weight, its formula, or a combination thereof. In some instances, the polydimethylsiloxane fluid may have the following characteristics as shown in Table 1:

TABLE 1

| Viscosity | Approximate Molecular Weight[1] | Approximate Average Number of Monomer Units in the Polymer[1] |
|---|---|---|
| 3 Centistokes | 500 | 6 |
| 5 Centistokes | 800 | 9 |
| 10 Centistokes | 1200 | 13 |
| 20 Centistokes | 2000 | 27 |
| 30 Centistokes | 2600 | 35 |
| 50 Centistokes | 3800 | 50 |
| 100 Centistokes | 6000 | 80 |
| 200 Centistokes | 9400 | 125 |
| 350 Centistokes | 13,700 | 185 |

[1]The compositions of Examples herein, to the extent they contained a dimethicone fluid, were formulated utilitizing a Dow Corning DC200 series fluid, which is believed to have had average molecule weights and average number of monomer subunits falling within the approximate values of above-described table.

One skilled in the art will know that dimethicones with higher molecular weights will generally have lower solubility in many organic emollients than those with lower molecular weights, so it is often possible to design a second oil phase that is insoluble in the first oil phase (less than or at most 5% solubility via the test method) by choosing a high molecular weight dimethicone or by creating a mixture of dimethicones that provides both the requisite solubility and desired feel on skin.

The second oil phase may also contain other dimethicone soluble emollients such as, but not limited to, cyclic volatile silicones, linear volatile silicones, isoparaffins, alkyl dimethicones, capryl methicone, dimethiconol and high molecular weight silicone gums.

The emollients in the second oil phase may comprise from about 5% to about 30%, by weight, of the antiperspirant or deodorant composition. In some embodiments, the emollients in the second oil phase may comprise from about 3% to about 10%, by weight, of the antiperspirant or deodorant composition.

Emulsifiers, Surfactants and Co-Emulsifiers

The multiple oil phases in the oil in water emulsion may also comprise one or more of the following: emulsifiers, surfactants, and co-emulsifiers. These materials may perform several functions in the foaming antiperspirant and deodorant composition including, but not limited to, stabilizing the oil in water emulsion, reducing the surface tension of the water phase to allow foam formation, solubilization of the blowing agent, and stabilization of the foam on the applicator surface. Choice of these materials is dependent on the composition of the oil in water emulsion, particularly the compositions of the emollients that are in the first and second oil phases. Moreover, it is desirable to choose materials that can provide multiple benefits, such as emulsion stabilization and foam creation/stabilization. Furthermore, the choice of any emulsifier, surfactant, or co-emulsifer must not interfere with the performance of the antiperspirant or deodorant actives used in the antiperspirant or deodorant composition. For example, the use of some anionic surfactants can interfere with efficacy of cationic aluminum antiperspirant actives via the formation of insoluble ion pairs. Lastly, it is appreciated that different oil phase emollients will require different emulsifiers, surfactants, or co-emulsifiers to create a stable multiphase oil in water emulsion. Said differently, the different oil phases that are insoluble in one another may require different emulsifiers and co-emulsifiers to stabilize each emulsion phase in the oil in water emulsion. Often, it may be convenient to add the appropriate emulsifiers, surfactant, and or co-emulsifer with each oil phase emollient to assure that they are associated with the desired oil phase.

An emulsifer or surfactant used to stabilize an emulsion may be chosen based on the required HLB (hydrophilic lipophilic balance) of the oil phase emollients. The HLB of a surfactant is a measure of the ratio of the hydrophobic to the hydrophilic portion of the surfactant or emulsifier. Choice of the desired HLB for an emollient is dependent on the emollient or emollient blend polarity and structure. The use of the HLB system for emulsion formulation is discussed in the following references:

1. Griffin WC; Calculation of HLB Values of Non-Ionic Surfactants, *Journal of the Society of Cosmetic Chemists;* 1954. Vol. 5, pp 249-235
2. Vaughan, C. D. Rice, Dennis A.; Predicting O/W Emulsion Stability by the "Required HLB Equation"; *Journal of Dispersion Science and Technology;* 1990. Vol. 11 (1), pp 83-91.

Any known oil in water emulsifier, surfactant, or co-emulsifer can be used in the foaming antiperspirant or deodorant compositions herein, provided that they stabilize the multiple emulsions and do not interfere with the delivery or action of the antiperspirant or deodorant actives. Suitable classes of emulsifiers and surfactants include anionic, cationic and nonionic materials. Moreover, for some oil phase emollients, polymeric emulsifiers and surfactants are suitable. In some embodiments, nonionic emulsifiers, surfactants, and co-emulsifiers are preferred to prevent interaction with any charged antiperspirant active (i.e. aluminum chlorohydrate) or deodorant active (i.e. benzethonium chloride).

Emulsifer, surfactant, and coemulsifer concentrations will vary based on composition and level of each oil phase emulsion, however it is generally found to be desirable to not have excess emulsifier, surfactant and coemulsifer to prevent skin irritation. Total levels of emulsifier, surfactant, and coemulsifer should be less than about 12%, more preferably less than about 10% and most preferrably less than about about 7%, by weight of the antiperspirant or deodorant composition.

Suitable nonionic emulsifiers and surfactants include, but are not limited to, linear saturated and unsaturated C12 to C30 primary alcohols that are etherified with 1 to 100 ethylene oxide units per molecule. More preferred nonionic emulsifiers laureth, trideceth, myristeth, ceteth, ceteareth steareth, arachideth, and beheneth, having respectively 1 to 100 ethylene oxide units per molecule. Some examples of preferred nonionic emulsifiers and surfactants include, but are not limited to, steareth-1, steareth-2, steareth-3, steareth-20, steareth-21, steareth-100, ceteareth-10, ceteareth-20 ceteareth-30, ceteth-1, ceteth-2, ceteth-3, ceteth-10, myristeth-1, myristeth-2, laureth-4, beheneth-2, beheneth-3, and beheneth-5, behenth-10 and beheneth-25.

In some embodiments of the present invention, steareth-2 and steareth-21 are preferred emulsifiers or surfactants. Preferred weight ratios of steareth-21 to steareth-2 range from about 0.2 to about 5, more preferably from about 0.2 to about 2. In some embodiments of the present invention Ceteth-10 and Laureth-4 are preferred emulsifiers or surfactants.

Suitable anionic emulsifiers and surfactants include, but are not limited to, ammonium lauryl sulfate, sodium laureth sulfate, sodium oleyl succinate, ammonium lauryl sulfosuccinate, sodium dodecylbenzenesulfonate, ammonium laureth, sodium N-lauryl sarcosinate, or sodium lauryl sulfate.

Suitable cationic emulsifiers and surfactants include, but are not limited to, distearyldimonium chloride, behentrimonium chloride and palmitamido-propyltrimonium chloride.

Suitable co-emulsifiers include, but are not limited to, fatty alcohols such as stearyl alcohol, cetyl alcohol, and cetearyl alcohol. However, in some embodiments, the emulsion may not comprise a fatty alcohol, as fatty alcohols can increase the viscosity of the oil in water emulsion to a level that is difficult to mix with certain blowing agents, making them undesirable. One potential example of this would be if the fatty alcohol increased the viscosity about about 10,000 cst, which would be very difficult to mix with a water insoluble blowing agent, such as butane.

In some embodiments, ethoxylated fatty alcohols are preferred emulsifiers due to their ability to both stabilize the emulsion and create stable foams.

Fragrance

One or more fragrance materials are included to help cover or mask malodors resulting from perspiration or which otherwise provide the compositions with the desired perfume aroma. These fragrance materials may include any perfume or perfume chemical suitable for topical application to the skin.

The concentration of the fragrance in the foaming antiperspirant or deodorant compositions should be effective to provide the desired aroma characteristics or to mask malodor wherein the malodor is inherently associated with the composition itself or is associated with malodor development from human perspiration. Compositions of the present invention may comprise fragrances selected from the group consisting of free perfumes, encapsulated perfumes, and mixtures thereof. The total perfume may include one or more individual perfume chemicals provided that the perfume can emit a detectable perfume odor or can mask or help to mask odors associated with perspiration. Generally, the deodorant compositions of the present invention may comprise the total perfume at concentrations ranging from about 0.05% to about 10%, preferably from about 0.5 to about 5% and more preferably from about 1 to about 4%. As previously discussed the choice of fragrance level and the emollient level both in the first oil phase are often related by desired emollient to fragrance weight ratios of from about 1:1 to about 10:1, and more preferably, from 3:1 to about 7:1. The fragrance that is in the antiperspirant and/or deodorant composition may be entirely in the first oil phase and may be solubilized in the first oil phase.

Nonlimiting examples of fragrance materials suitable for use as a free perfume or an encapsulated perfume include any known fragrances in the art or any otherwise effective fragrance materials. Typical fragrances are described in Arctander, Perfume and Flavour Chemicals (Aroma Chemicals), Vol. I and II (1969) and Arctander, Perfume and Flavour Materials of Natural Origin (1960). U.S. Pat. No. 4,322,308, issued to Hooper et al., Mar. 30, 1982 and U.S. Pat. No. 4,304,679, issued to Hooper et al., Dec. 8, 1981 disclose suitable fragrance materials including, but not limited to, volatile phenolic substances (such as iso-amyl salicylate, benzyl salicylate, and thyme oil red), essence oils (such as geranium oil, patchouli oil, and petitgrain oil), citrus oils, extracts and resins (such as benzoin siam resinoid and opoponax resinoid), "synthetic" oils (such as Bergamot™ 37 and Bergamot™ 430, Geranium™ 76 and Pomeransol™ 314); aldehydes and ketones (such as B-methyl naphthyl ketone, p-t-butyl-A-methyl hydrocinnamic aldehyde and p-t-amyl cyclohexanone), polycyclic compounds (such as coumarin and beta-naphthyl methyl ether), esters (such as diethyl phthalate, phenylethyl phenylacetate, nonanolide 1:4).

Suitable fragrance materials may also include esters and essential oils derived from floral materials and fruits, citrus oils, absolutes, aldehydes, resinoids, musk and other animal notes (e.g., natural isolates of civet, castoreum and musk), balsamic, and alcohols (such as dimyrcetol, phenylethyl alcohol and tetrahydromuguol). For example, the present invention may comprise fragrances selected from the group consisting of decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, amylcyclohexanone, and mixtures thereof.

Antiperspirant and Deodorant Actives

The water phase of the water in oil emulsion generally includes water and an antiperspirant active and/or a deodorant active dissolved in water. The concentration of the antiperspirant active and/or deodorant actives in the composition should be sufficient to provide the finished antiperspirant or deodorant composition with the desired perspiration wetness and/or odor control benefits.

Exemplary antiperspirant active concentrations range include from about 0.1% to about 26%, from about 1% to about 20%, and from about 2% to about 10%, by weight of the composition. All such weight percentages are calculated on an anhydrous metal salt basis exclusive of water and any complexing or buffering agent such as, for example, glycine, glycine salts or other amino acids and any stabilizing agents such as calcium chloride, calcium salts, or strontium salts.

Preferred aluminum salts are those having the general formula $Al_2(OH)_{6-a}X_a$ wherein X is Cl, Br, I or $NO_3$, and a is about 0.3 to about 5, preferably about 0.8 to about 2.5. Preferred actives in this group include, but are not limited to, aluminum chlorohydrate (ACH) wherein a is from about 1 and the mole ratio of Al/Cl is from about 1.9 to about 2.1, Aluminum sesquichlorohydrate (ASCH) wherein a is from about 1.05 to about 1.61 and the mole ratio of Al/Cl is from about 1.26 to about 1.89, and aluminum dichlorohydrate (ADCH) wherein a is from about 1.6 to about 2.2 and the mole ratio of Al/Cl is from about 0.9 to about 1.25.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 0.5 to 2, preferably about 1.0 to about 1.9. The aluminum-zirconium salts employed in the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. Aluminum-zirconium chlorohydrate is referred to as "ACH/ZHC" or as "AZCH" herein.

The aluminum and aluminum-zirconium salts of the present invention may be of the enhanced efficacy type. The term "enhanced efficacy salts" means antiperspirant salts which, when reconstituted as 10% aqueous solutions (or if already a solution, diluted with water to about 10% salt concentration in solution), produce an HPLC chromatogram (as described, for example, in U.S. Pat. No. 5,330,751, which is incorporated herein by reference) wherein at least 40%, preferably at least 50%, of the aluminum is contained in two successive peaks, conveniently labeled peaks 4 and 5, and wherein the ratio of the area under peak 4 to the area under peak 3 is at least 0.35, preferably at least 0.5, and more preferably at least 0.9 or higher. Most preferred are salts which exhibit an HPLC peak 4 to peak 3 area ratio of at least 0.35 when measured within two hours of preparation, and which retain a peak 4 to peak 3 area ratio of at least 0.35, preferably at least 0.7, when stored as an aqueous solution of at least 20% salt concentration for one month. Especially preferred are salts wherein at least 25%, more preferably at least 40%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "ACH" herein. Enhanced efficacy aluminum-zirconium chlorohydrate is referred to as "ACH'/ZHC" or as "AZCH'" herein.

The ACH and AZCH salts used in the present invention may also include soluble calcium salts. Soluble calcium salts are those calcium salts that are soluble in water or that dissolve in the aqueous solution of antiperspirant salt (i.e. a solution of the aluminum salt and/or zirconium salt). Calcium salts which may be utilized are any of those which do not otherwise interfere with the solubility or effectiveness of the antiperspirant salt. Preferred calcium salts include calcium chloride, calcium bromide, calcium nitrate, calcium citrate, calcium formate, calcium acetate, calcium gluconate, calcium ascorbate, calcium lactate, calcium glycinate and mixtures thereof. Calcium carbonate, calcium sulfate and calcium hydroxide may also be used because they will dissolve in an aqueous solution of the antiperspirant salt. The amount of calcium salt utilized in a AZCH salt should be that amount which provides a Ca:Al+Zr weight ratio of about 1:1 to about 1:28, preferably about 1:2 to about 1:25. Generally, the aqueous AZCH solution will contain about 0.3 to about 3% by weight Ca, preferably about 0.5 to about 2.5% by weight Ca, most preferably about 1.0 to about 2.0% by weight Ca, based on the weight of the entire composition. These amounts of calcium in the AZCH aqueous may be obtained by the inclusion of about 1% to about 7% by weight of calcium chloride, nitrate or sulfate or similar salts.

The ACH and AZCH salts used in the present invention may also contain a water soluble amino and/or hydroxy acid which is effective in increasing and/or stabilizing the HPLC peak 4:3 area ratio of the antiperspirant salt. Such acids include amino- and/or hydroxy-substituted lower alkanoic acids (including substituted derivatives thereof), preferably where the amino or hydroxy group is located on the α-carbon (i.e. the same carbon to which the carboxy group is attached). The lower alkanoic acid will generally have 2 to 6, preferably 2 to 4, carbon atoms in the alkanoic acid chain. Typical amino and/or hydroxy substituted lower alkanoic acids include any of the amino acids such as glycine, alanine, valine, leucine, isoleucine, P-alanine, serine, cysteine, β-amino-n-butyric acid, γ-amino-n-butyric acid, etc. and hydroxy acids such as glycolic acid and lactic acid. These amino and/or hydroxy substituted lower alkanoic acids may also contain various substituents which do not adversely affect their activity. The preferred amino and/or hydroxy substituted lower alkanoic acids are glycine, alanine, and glycolic acid, with glycine being most preferred. The amount of amino acid or hydroxy acid utilized in an AZCH salt should be that amount which provides an acid:Al+Zr ratio of about 2:1 to about 1:20, preferably about 1:1 to about 1:10, and most preferably about 1:2 to about 1:7. Generally, the aqueous AZCH salt solution will contain about 1% to about 15% by weight amino acid or hydroxy acid, preferably about 2% to about 10% by weight, based on the weight of the entire composition. The amino and/or hydroxy acid need not be separately added to the composition, but may be included as part of the antiperspirant salt complex such as, for example, Al—Zr-Gly salts (e.g. aluminum-zirconium tetrachlorohydrate-gly). The glycine content of such salts may be adjusted to provide the aforementioned ratio. The amino and/or hydroxy acid may also be added as a salt, particularly the calcium salt such as, for example, calcium glycinate.

In some embodiments, a preferred active is an aqueous solution of ADCH that also contains calcium chloride and glycine. The preferred ADCH with calcium chloride and glycine is further characterized by having more than 50% peak 4 and 5 as measured by HPLC, a Al:Cl molar ratio of about 0.9 to about 1.25, an Al to glycine wt ratio of about 1.7 to 7.7, and calcium to glycine wt ratio of about 0.1 to about 1.5. In some embodiments a preferred active is an aqeuous solution of ASCH that also contains calcium chloride and glycine. The preferred ASCH with calcium chloride and glycine is further characterized by having more than 35% peak 4 and 5 as measured by HPLC, a Al:Cl molar ratio of about 1.26 to about 1.89, an Al to glycine wt ratio of about 4 to 10, and calcium to glycine ratio of about 0.1 to about 1.5.

The foaming antiperspirant or deodorant compositions provided herein may comprise a non-aluminum antiperspirant active. Suitable non aluminum antiperspirant actives include, but are not limited to, oxybutynin chloride, chitosan, PVM/MA polymers, calcium channel blockers, gingerol, liquid fatty acid and metal ion combinations, magnesium gluconate, silicic acid, silicic acid salts, and vicinol diols such as propylene glycol.

The foaming antiperspirant and/or deodorant compositions provided herein may comprise a deodorant active, alternatively meaning that a deodorant active is substituted for an antiperspirant active or used in addition to the antiperspirant active. Some deodorants may not have an antiperspirant active and/or may be substantially free or free of aluminum.

Suitable deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

In some embodiments, antibacterials (deodorant actives) may be selected from the group consisting of 2-Pyridinol-N-oxide (piroctone olamine), lupamin, beryllium carbonate, magnesium carbonate, calcium carbonate, magnesium hydroxide, magnesium hydroxide and magnesium carbonate hydroxide, partially carbonated magnesium hydroxide, potassium carbonate, potassium bicarbonate, sodium carbonate, sodium sesquicarbonate, baking soda, hexamidine, zinc carbonate, thymol, polyvinyl formate, salicylic acid, niacinamide and combinations thereof.

The concentration of the optional other active(s) may range, individually or cumulatively, from about 0.001%, from about 0.01%, of from about 0.1%, by weight of the composition to about 20%, to about 10%, to about 5%, or to about 1%, by weight of the composition.

Blowing Agents

Blowing agents are materials that are capable of creating the cellular structure or bubbles that comprise a foam. These materials expand upon release from the package, thereby creating bubbles that form the cellular structure of the foam. Any blowing agent capable of converting the oil in water emulsion from a liquid to a foam is suitable for use in the present invention. This includes, but is not limited to, liquified gases and compressed gasses. It is appreciated that the type, pressure, and level of the blowing agent should not result in aerosolization of the product or composition such that the product or composition becomes airborne during the dosing process. Further it is appreciated that the choice of type, pressure, and amount of the blowing agent will be related to the type of valve used to release the foaming antiperspirant and deodorant product/composition, the flow path to the application surface, and the size of the container that holds the foaming antiperspirant and deodorant product prior to its release. The inventors have found that foam creation and delivery to an application surface is best achieved with blowing agent concentrations of at most about 15%, by weight of the composition. In some embodiments, foam creation and delivery is achieved with at most about 10% blowing agent, and in others it is achieved with at most about 5% blowing agent, by weight of the composition.

Some suitable liquidifed gas blowing agents may have a boiling point (at atmospheric pressure) within the range of from about −45° C. to about 5° C. Some suitable liquidifed gas blowing agents may include chemically-inert hydrocarbons such as propane, n-butane, isobutane and cyclopropane, and mixtures thereof, as well as halogenated hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Some commercially available liquidifed gas blowing agents suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), Br-46 (a mixture of butane, propane and isobutane), HFO1234 (trans-1,3,3,3-tetrafluoropropene) and 152A (1,1 difluoroethane).

Suitable compressed gas blowing agents include but are not limited to such as nitrogen, air and carbon dioxide, nitrous oxide, argon, helium, and oxygen.

In some embodiments, water soluble blowing agents such as, but not limited to, dimethyl ether, carbon dioxide or nitrous oxide, and combinations thereof, will be employed. Water soluble blowing agents may reduce the mixing required to incorporate the blowing agents into the oil in water emulsion. In some other embodiments, a water insoluble blowing agent such as, but not limited to, A46, A31, or nitrogen may be employed to provide a desired foam appearance. However, it is appreciated that incorporation of an water insoluble blowing agent into the dispersed oil phase can require substantial mixing and the unincorporated material will remain segregated from the oil in water emulsion. One of the challenges in the use of blowing agents in the foaming antiperspirants and deodorants of the current invention is the uniformity of foam density and appearance throughout the life of the can. For example, a composition with a liquid gas blowing agent will maintain the pressure in the can during its use by converting liquid blowing agent to gaseous blowing agent in the head space above the oil in water emulsion in the sealed container. This process reduces the amount of liquid blowing agent in the oil in water emulsion that provides the foaming benefit, often resulting in a runnier foam when more than 75% of the initial product or composition has been dispensed. Moreover, in some embodiments, this effect can substantially reduce the dose of foam released between the first and last dose of the product. Inconsistent dosing from the first to last dose of the product can result in consumer frustration and a reduction in efficacy. Surprisingly, the present inventors have found that employing two blowing agents, one water soluble and one water insoluble, overcomes this challenge. The second, water insoluble blowing agent is able to hold the first blowing agent in solution so that its concentration stays high. Moreover, this combination of two blowing agents also provides a visually more desirable foam by creating small bubbles that create a foam with a matte finish, which looks drier and more desirable to some consumers.

In the present invention, a water soluble blowing agent has a water solubility of at least 0.1 weight percent in water at 20° C. Conversely, water insoluble blowing agents have a water solubility of at most 0.01 weight percent in water at 20° C. Examples of the water solubility of some blowing agents are shown in Table 2.

TABLE 2

| Blowing agent | Water solubility at 20° C. (weight percent) |
|---|---|
| Butane | <0.01% |
| Isobutane | <0.01% |

TABLE 2-continued

| Blowing agent | Water solubility at 20° C. (weight percent) |
|---|---|
| Propane | <0.01% |
| Dimethyl ether | 7% |
| 1,1 difluoroethane | 0.2% |
| Nitrogen | <0.01 |
| Helium | <0.01 |
| Carbon dioxide | 0.8% |
| Nitrous oxide | 0.12 |

Figure 2A:
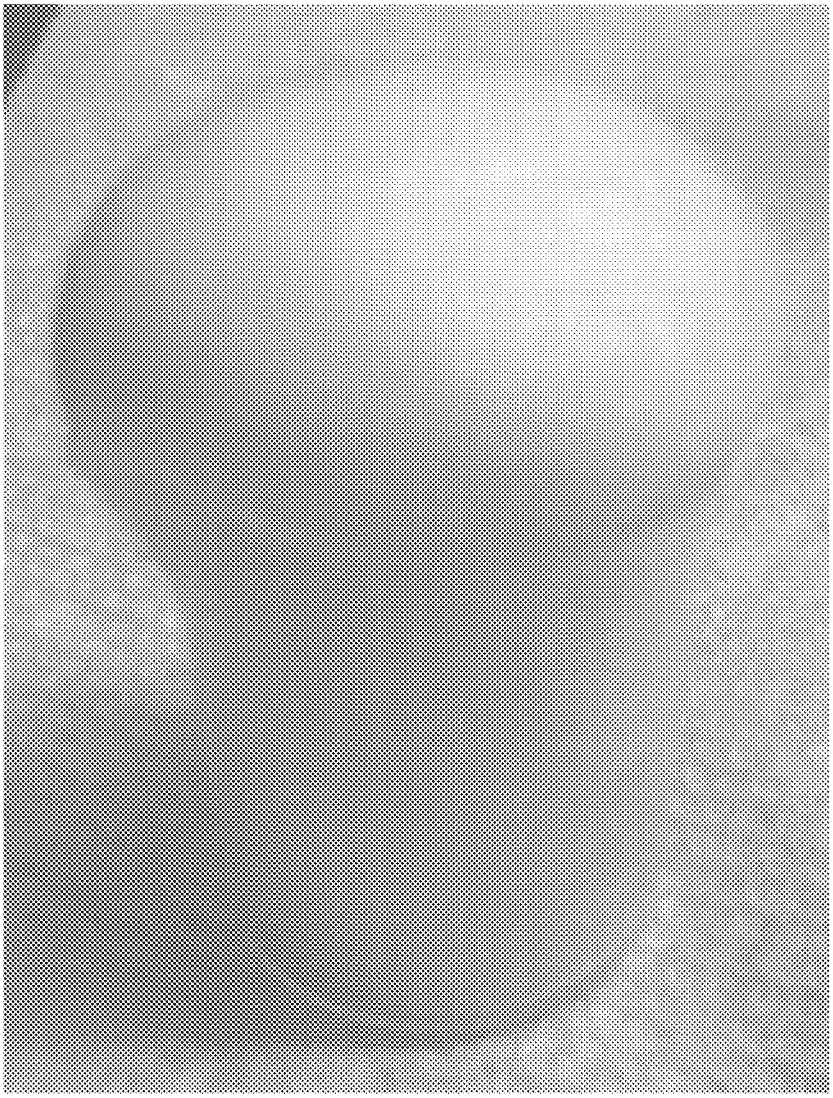
FIGS. 2*a* and 2*b* are photographs showing the impact of two blowing agents vs one blowing agent.
Figure 2B:
Figure 3:
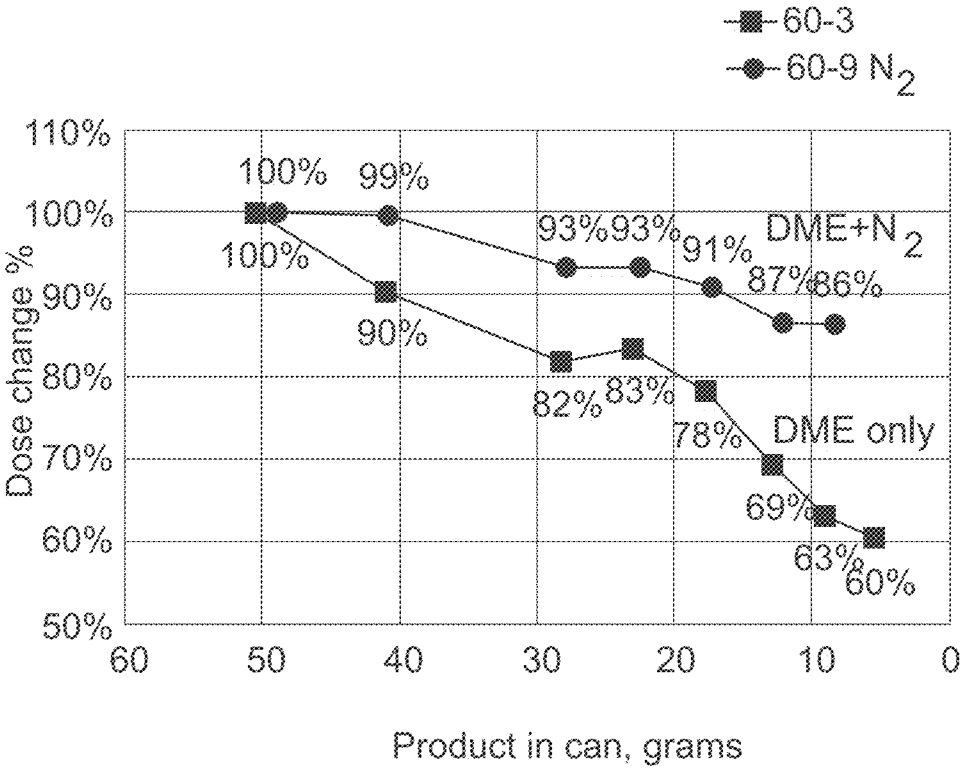
FIG. 3 is a graph showing the percent of initial dose for two compositions that vary only in their blowing agents.

One example of two blowing agents is a blend of dimethyl ether (water soluble) and nitrogen (water insoluble). As can be seen from FIGS. 2*a* and 2*b*, a blend of these materials creates a more desired foam appearance. FIG. 2*a* shows a dispensed foam composition comprising two blowing agents, dimethyl ether and nitrogen. FIG. 2*b* shows the same foam composition, other than it comprises dimethyl ether alone. The foam in FIG. 2*a* is more desirable to consumers than the foam in FIG. 2*b*, as the FIG. 2*a* foam has smaller bubbles and looks drier. Moreover, when the blend is employed in a package that includes a can and a metered aerosol valve, the blend results in a more uniform dosage delivery throughout the life of can. FIG. 3 is a graph showing the percent of initial dose for two compositions that are the same other than the blowing agent(s), in the same type of can and metered valve. The metered valve should release the same volume out of the can with each dispense. The bottom line shows the composition comprising only DME (dimethyl ether) as a blowing agent, while the top line shows a blowing agent of DME and nitrogen. As can be seen from the graph, the composition comprising the two blowing agents of DME and nitrogen maintains a more stable amount of the composition dispensed for each dose throughout the life of the can. That is, each successive dose is relatively close to 100% as compared to successive doses from the can with the single blowing agent. This means the two blowing agents provide a more consistent amount of composition dispensed for each dose. This results in a more consistent dosage and experience of the composition by the consumer throughout the life of the can. The composition comprising only DME over time releases less volume of composition with each dispense, because the pressure provided by the single blowing agent becomes too low to release a full dose.

Examples

| | Material | A | B | C | D | E | F | G | H | I |
|---|---|---|---|---|---|---|---|---|---|---|
| Water Phase | Aluminum dichlorohydrate | 12 | 12 | 17.5 | 25 | | | 12 | 12 | |
| | Calcium chloride | 0.3 | 0.3 | 0.5 | | 0.3 | | 0.3 | 0.3 | |
| | Glycine | 1.3 | 1.3 | 1.9 | | 1.3 | | 1.3 | 1.3 | |
| | Water | OS | OS | OS | OS | OS | OS | OS | OS | OS |
| | Aluminum Sesquichlorohydrate | | | | | 12 | | | | |
| | Oxybutynin chloride | | | | | | 3 | | | |
| | Piroctone Olamine | | | | | | | | | 0.5 |
| First Oil Phase | | | | | | | | | | |
| | Steareth-2 | 2.2 | 3.2 | 3.2 | 3.2 | 3.2 | 3.2 | 3.2 | 3.2 | 3.2 |
| | Steareth-21 | 1.5 | 1.5 | 1.5 | 1.5 | 1.5 | 1.5 | 1.5 | 1.5 | 1.5 |
| | Cetearyl Alcohol | 1.0 | | | 1.0 | | | | | |
| | PPG-15 Stearyl ether | 8.4 | 18.5 | 18.5 | 16.5 | 10 | 15.5 | 18.5 | 8.4 | 15.5 |
| | PPG-14 butyl ether | | | | | 5.5 | | | | |
| | Fragrance | 2.8 | 2.8 | 2.8 | 2.8 | 2.8 | 2.8 | 2.8 | 2.8 | 2.8 |

-continued

| | Material | A | B | C | D | E | F | G | H | I |
|---|---|---|---|---|---|---|---|---|---|---|
| Second Oil Phase | | | | | | | | | | |
| | 100 cst dimethicone | 13.6 | 5.5 | 5.5 | 5.5 | 5.5 | | 5.5 | 13.6 | |
| | 50 cst dimethicone | | | | | | 5.5 | | | 5.5 |
| | 10 cst dimethicone | | | | | | | | | |
| | Dimethicone and Dimethiconol* | | | | | 3 | 3 | | | 3 |
| | Laureth-4 | 0.2 | 0.2 | 0.2 | 0.2 | 0.2 | 0.2 | 0.2 | 0.2 | 0.2 |
| | Ceteth-10 | 0.4 | 0.4 | 0.4 | 0.4 | 0.4 | 0.4 | 0.4 | 0.4 | 0.4 |
| Blowing Agent | Dimethyl ether | 9.0 | 7.0 | 7.0 | 9 | 7.0 | 7.0 | | 5.0 | 7.0 |
| | Nitrogen | | 0.5 | 0.5 | | 0.5 | 0.5 | 0.5 | | 0.5 |
| | Carbon dioxide | | | | | | | 2.0 | | |
| | A46 | | | | | | | | 4.0 | |

*Xiameter PMX-1503 Fluid

Method of Making

The foaming antiperspirant and deodorant compositions of the present invention, such as Inventive Examples A-I, can be made by any known method that creates the multi-phase oil in water emulsion, adds blowing agent to the oil in water emulsion, either during or after the emulsion is sealed in a pressurizable container with an aerosol valve, and then affixing a way to actuate the valve, thereby releasing foam for application to the axillia. One method that is found to be convenient is as follows: To a main mix tank, the fraction of water not included in the aqueous solution of the active is heated to about 65° C. In a separate container, all the components of the first oil phase are combined, heated to about 65° C. with agitation, and held at that temperature until all components are molten. In a third container, all the components of the second oil phase are combined, heated to about 65° C. with agitation, and held at that temperature until all components are molten. Next, the molten first oil phase is slowly added to the main mix tank with agitation and allowed for mix until a uniform emulsion is created. Then the molten second oil phase is slowly added to the main mix tank with agitation and allowed for mix until a uniform emulsion is created. The batch is then cooled and milled at about 55° C. to reduce the emulsion particle size with an appropriate rotor stator mill. In the last step of emulsion making, if the composition comprises an antiperspirant active, the aqueous solution of antiperspirant active is added which cools the batch, typically to near 40° C., at which point the emulsion is subjected to a final milling to assure a uniform particle size. One skilled in the art will appreciate the ability or need to alter the temperatures and mix times in this example based on the desired composition of the oil in water emulsion.

After the emulsion is formed, it is added to a pressurizable container, such as, but not limited to, an epoxy lined aluminum aerosol can or pressurizable plastic aerosol container. In the next step, the container is sealed with an appropriate aerosol valve to contain the emulsion and any blowing agents under pressure. Either standard flow aerosol valves or metered aerosol valves can be employed depending on the desired actuation and application method. For metered valves, the dispense volume may be about 100 to about 400 microliters, which are a convenient way to control dosing to an application surface. The blowing agent can be added to the container either during or after the valve is affixed and sealed onto the pressurizable container. Liquified gas propellants are most conveniently added to pressurizable containers through the valve after being sealed. Compressed gases are often added during the sealing process using an under the cup (UTC) aerosol filler, which both adds the blowing agent and seals the valve on the pressurizable container. For products comprising an oil in water emulsion, a liquified gas blowing agent, and a compressed gas blowing agent, it is often convenient to first add the emulsion to the pressurizable container, add the compressed gas using a UTC filler that also seals the valve onto pressurizable container, and then add the liquified gas blowing agent to the pressurized container through the aerosol valve.

Test Method for Oil Phase Emollient Solubility

Figure 4:
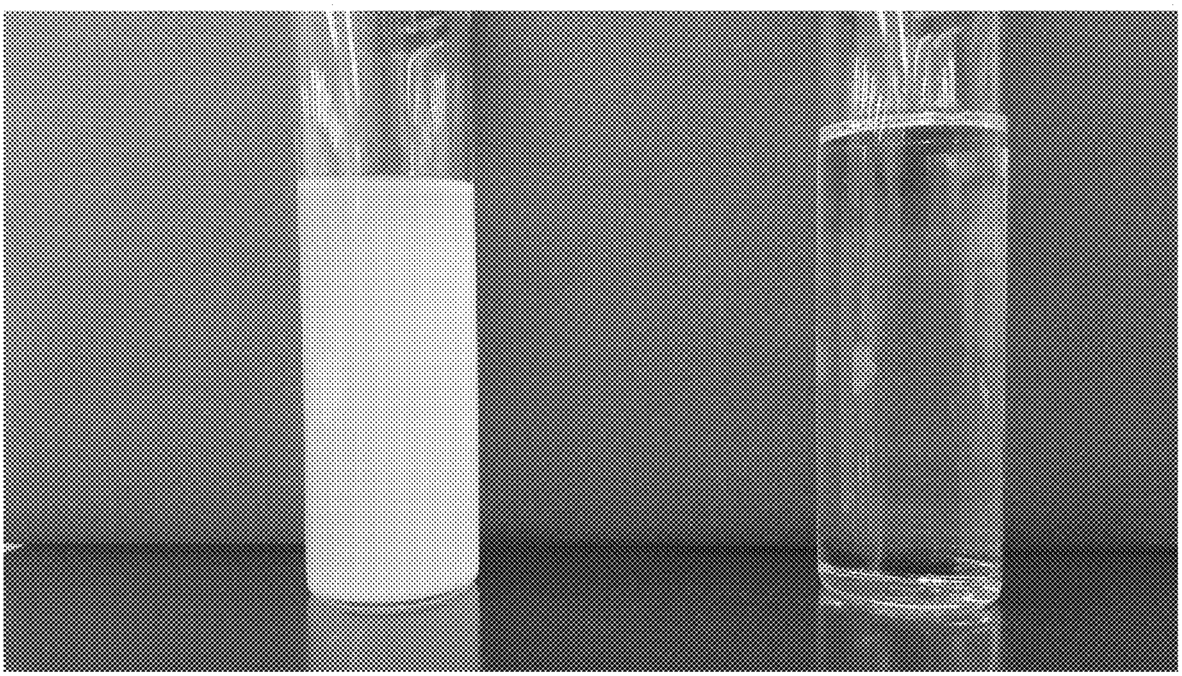
FIG. 4 is a photograph of a passing and a failing test of oil phase emollient solubility.

To test for solubility of the second oil phase emollients in the first oil phase emollients at a 5% level, or said differently, to test that the second oil phase emollients have less than or at most 5% solubility in the first oil phase emollients, add 19 grams of the first oil phase emollients and 1 gram of the second oil phase emollients to an 8-dram vial. Vigorously shake the vial for approximately 30 seconds to allow mixing and then allowing the vial to set unmoved for 5 minutes. After 5 minutes, a single-phase clear solution indicates too much solubility and a test failure, meaning there is a higher solubility than 5% of the second oil phase emollients in the first oil phase emollients. The formation of something other than a single-phase solution indicates a test passing result, meaning that there is at most a 5% solubility of the second oil phase emollients in the first oil phase emollients. Passing observations can include, but are not limited to, the formation of two clear solutions layers, a hazy and a clear layer, two hazy layers, a single hazy layer, a single opaque layer, or any other condition that one skilled in the art would deem to not be a single phase clear solution. Examples of passing and failing solutions are shown in FIG. 4. The passing solution on the left comprises a first oil phase emollient of PPG-15 stearyl ether and a second oil phase emollient of 50 cst dimethicone. The failing solutions on the right comprise a first oil phase emollient of Isopropyl myristate and a second oil phase emollient of 5 cst dimethicone. One skilled in the art will understand that testing for solubility at a lower concentrations, or that testing for various levels of solubility (e.g., 1% solubility or 0.5% solubility), can be done by appropriately adjusting the weights of the two oil phase emollients in the 8-dram vial, then mixing and evaluating the vial in the manner disclosed above.

Examples/Combinations

A. A foaming antiperspirant or deodorant composition comprising: a. an oil in water emulsion comprising: i. a first oil phase comprising one or more emollients; ii. a second oil phase comprising one or more emollients; wherein the second oil phase emollients have at most 5% solubility in the first oil phase emollients; iii. an antiperspirant or deodorant active; iv. one or more nonionic emulsifier; and v. a fragrance; and b. at most about 15%, by weight of the composition, of a blowing agent.

B. The composition of paragraph A, wherein the fragrance is in the first oil phase.

C. The composition of any one of paragraph A or B, wherein the fragrance is soluble in the first oil phase.

D. The composition of paragraphs A to C, wherein the first oil phase comprises an organic emollient.

E. The composition of paragraph D, wherein the weight ratio of the organic emollient in the first oil phase to the fragrance is at least about 1:1.

F. The composition of paragraph D, wherein the weight ratio of the organic emollient to the fragrance is from about 1:1 to about 10:1.

G. The composition of paragraph D, wherein the weight ratio of the organic emollient to the fragrance is from about 3:1 to about 7:1.

H. The composition of any one of paragraphs A to G, wherein the second oil phase comprises a silicone.

I. The composition of paragraph H, wherein the silicone is a dimethicone with a viscosity of at least about 3 cst or mixture of dimethicones each with a viscosity of at least about 3 cst.

J. The composition of any one of paragraphs A to I, wherein the one or more nonionic emulsifier is selected from the group consisting of ethoxylated fatty alcohols, fatty alcohols, ethoxylated propoxylated fatty alcohols, ethoxylated fatty acids, and combinations thereof.

K. The composition of any one of paragraphs A to J, wherein the emulsion does not comprise a fatty alcohol.

L. The composition of any one of paragraphs A to K, wherein the composition is contained in a device, wherein the device comprises a metered valve.

M. The composition of any one of paragraphs A to L, wherein the blowing agent has a water solubility of more than 0.1 weight percent in water at 20° C.

N. The composition of any one of paragraphs A to M, wherein the blowing agent is selected from the group consisting of carbon dioxide, dimethyl ether, and mixtures thereof.

O. The composition of any one of paragraphs A to N, wherein the composition comprises at most about 10%, by weight of the composition, of a blowing agent.

P. The composition of any one of paragraphs A to 0, wherein the oil in water emulsion further comprises two or more ethoxylated surfactants.

Q. The composition of any one of paragraphs A to P, wherein the antiperspirant active is aluminum dichlorohydrate or aluminum sesquichlorohydrate.

R. A foaming antiperspirant or deodorant composition comprising: a. an oil in water emulsion comprising: i. a first oil phase comprising at least one liquid with a Hildebrand solubility parameter from about 14 to about 22 $(MPa)^{0.5}$; ii. a second oil phase comprising a liquid polydimethylsiloxane with a viscosity of about 3 to about 350 cst; iii. an antiperspirant or deodorant active; iv. one or more nonionic emulsifier; and v. a fragrance; and b. at most about 15%, by weight of the composition, of a blowing agent.

S. The composition of paragraph R, wherein the first oil phase liquid is an organic emollient; and wherein the weight ratio of the organic emollient to the fragrance is from about 3:1 to about 7:1.

T. A method of making a foaming antiperspirant or deodorant composition, comprising the following steps:

a. in a first vessel, heating water to at least about 65° C.;
b. in a second vessel, heating all components of a first oil phase until molten;
c. in a third vessel, heating all components of a second oil phase until molten;
d. adding the molten first oil phase to the first vessel and mixing until uniform;
e. adding the molten second oil phase to the first vessel and mixing until uniform;
f. milling the contents of the first vessel while at least at about 65° C.; and
g. adding antiperspirant and/or deodorant actives to the first vessel.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". All numeric values (e.g., dimensions, flow rates, pressures, concentrations, etc.) recited herein may be modified by the term "about", even if not expressly so stated with the numeric value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A foaming antiperspirant or deodorant composition comprising:

a. an oil in water emulsion comprising:
  i. a water phase;
  ii. a first oil phase comprising:
    from about 5% to about 30% of one or more emollients chosen from PPG-14 butyl ether, isopropyl myristate, or mixtures thereof;
    a non-ionic emulsifier;
  iii. a second oil phase comprising:
    an emollient comprising dimethicone having a viscosity of about 3 to about 350 cst;
    a non-ionic emulsifier;
    wherein the emollient of the second oil phase has at most 5% solubility in the one or more emollients of the first oil phase;
  iv. an antiperspirant and/or a deodorant active;
b. at most 15%, by weight of the composition, of a blowing agent comprising: a first blowing agent having a water solubility of more than 0.1 weight percent in water at 20° C.; wherein the first blowing agent is present in the water phase; and a second blowing agent having a water solubility of at most 0.01 weight percent at 20° C., wherein the second blowing agent holds the first blowing agent in the water phase.

2. The composition of claim 1, wherein the emulsion does not comprise a fatty alcohol.

3. The composition of claim 1, wherein the composition is contained in a device, wherein the device comprises a metered valve.

4. The composition of claim 1, wherein the oil in water emulsion further comprises two or more ethoxylated surfactants.

5. The composition of claim 1, wherein the composition comprises an antiperspirant active, and the antiperspirant active is aluminum dichlorohydrate and/or aluminum sesquichlorohydrate.

6. The composition of claim 1, wherein the composition comprises at most 10% of the blowing agent.

7. The composition of claim 1, wherein the composition comprises at most 5% of the blowing agent.

8. The composition of claim 1, wherein the second blowing agent is a compressed gas.

9. The composition of claim 8, wherein the compressed gas comprises nitrogen.

10. The composition of claim 1, wherein the second blowing agent is chosen from butane, isobutane, propane, nitrogen, helium, or mixtures thereof.

11. The composition of claim 10, wherein the first blowing agent is chosen from dimethyl ether, carbon dioxide, 1,1-difluoroethane, nitrous oxide, or mixtures thereof.

12. The composition of claim 1, wherein the first blowing agent comprises dimethyl ether and carbon dioxide;

and wherein the second blowing agent comprises nitrogen.

13. A foaming antiperspirant or deodorant composition comprising:

a. an oil in water emulsion comprising:

i. a water phase;

ii. a first oil phase comprising:

from about 5% to about 30% of one or more emollients chosen from PPG-14 butyl ether, isopropyl myristate, or mixtures thereof;

a non-ionic emulsifier chosen from steareth 2, steareth 21, or mixtures thereof;

iii. a second oil phase comprising:

an emollient comprising dimethicone having a viscosity of about 3 to about 350 cst;

a non-ionic emulsifier chosen from laureth 4, ceteth 10, or mixtures thereof;

wherein the emollient of the second oil phase has at most 5% solubility in the one or more emollients of the first oil phase;

iv. an antiperspirant and/or a deodorant active;

b. at most 15%, by weight of the composition, of a blowing agent comprising:

a first blowing agent comprising at least two water soluble blowing agents comprising dimethyl ether and carbon dioxide; wherein the dimethyl ether and carbon dioxide are in the water phase;

and a second blowing agent comprising nitrogen, wherein the nitrogen holds the first blowing agent in the water phase.

* * * * *